United States Patent [19]

Trott

[11] Patent Number: 5,729,904
[45] Date of Patent: Mar. 24, 1998

[54] WRENCHLESS COLLECT FOR SURGICAL BLADE

[75] Inventor: A. Frank Trott, Largo, Fla.

[73] Assignee: Linvatec Corporation, Largo, Fla.

[21] Appl. No.: 548,351

[22] Filed: Nov. 1, 1995

[51] Int. Cl.[6] ................................................ A61B 17/14
[52] U.S. Cl. ............................................ 30/339; 606/178
[58] Field of Search .......................... 30/392-394, 339,
30/166.3; 279/83, 86, 141; 83/697, 698.71,
699.21; 606/82, 178

[56] References Cited

U.S. PATENT DOCUMENTS

| | | | |
|---|---|---|---|
| 4,106,181 | 8/1978 | Mattchen | 83/699.21 |
| 4,294,013 | 10/1981 | Krieg | 30/392 |
| 4,386,609 | 6/1983 | Mongeon | 128/9 |
| 5,013,194 | 5/1991 | Wienhold | 408/2 |
| 5,237,884 | 8/1993 | Seto | 74/4 |
| 5,265,343 | 11/1993 | Pascaloff | 30/1 |
| 5,380,333 | 1/1995 | Meloul et al. | 606/1 |
| 5,383,785 | 1/1995 | Brugger | 433/8 |
| 5,458,346 | 10/1995 | Briggs | 30/392 |

FOREIGN PATENT DOCUMENTS 2 195 274  4/1988  United Kingdom.

Primary Examiner—Douglas D. Watts
Attorney, Agent, or Firm—Gene Warzecha

[57] ABSTRACT

A wrenchless collet for attaching a surgical saw blade to an oscillating handpiece. The collet is provided within a housing attached to the handpiece and contains a clamping means for holding the blade and a bi-stable operating mechanism capable of holding the clamping means in either an open position to receive the blade or in a closed position to hold the blade for use with the handpiece. The bi-stable operating mechanism is activated into either position by simply being pushed in one direction or another. In one embodiment, the bi-stable operating mechanism comprises a shaft which may be positioned to one axial extreme or the other and which is held in the chosen position by a spring which frictionally engages the collet housing to maintain the clamping means in either an open or closed position.

13 Claims, 17 Drawing Sheets

WRENCHLESS COLLECT FOR SURGICAL BLADE

BACKGROUND OF THE INVENTION

1. Field of the Invention

The present invention relates to blade attachment mechanisms for surgical saws. More particularly, the invention relates to wrenchless chuck or collet which can secure a surgical device such as a saw blade to a drive means without any additional tools.

2. Description of the Prior Art

It is often necessary to use powered tissue cutting tools in order to perform surgical procedures. Such tools generally comprise a handpiece which cyclically moves a tissue cutting device such as a blade or burr in some oscillating or reciprocating manner. The handpiece generally includes a pneumatic or electric drive motor having an output shaft to which the cutting device is attached, the shaft being axially aligned with a drive axis of the handpiece. As used herein, the term "drive axis" refers to the axis of the motor output shaft through which power is delivered from the motor. The handpiece may be a "pencil" type handpiece in which the body is elongated and the drive axis is aligned with the axis of the body or a pistol-grip type of handpiece in which the drive axis is aligned in a chosen direction relative to the grip. The drive motor of the handpiece produces a driving force which reciprocates the output shaft and cutting device either longitudinally, i.e. linearly along the drive axis (like a saber saw), or arcuately in a plane perpendicular to the drive axis. Handpieces utilizing the former type of action are generally referred to as reciprocating saws while those utilizing the latter action are generally referred to as oscillating saws. In some cases an oscillating saw may transfer the oscillating drive motion so that it is cyclical within a plane parallel to the axis of the elongated body of the handpiece. A sagittal saw is a type of oscillatory saw in which the cyclical reciprocating action is in a plane aligned with the drive axis.

In all instances, numerous tissue cutting blades or burrs or other devices (all collectively referred to herein as "blades") are adapted to be secured to the handpiece via a chuck or collet mechanism which is utilized to selectively attach and release a desired blade. A variety of different cuts can be made with a single saw depending upon the shape of the blade. For oscillating saws, the blades are often in the form of a flat, elongated body having a cutting edge (e.g. teeth, abrader, etc.) at one end and a hub at the other end, the hub being shaped and adapted to fit the particular collet. Such flat blades are used to make cuts in a plane perpendicular to the drive axis. An oscillating saw may also be used for effecting cuts in a plane parallel to the handpiece axis by attaching a transverse hub to a flat blade.

Many blade collets utilize a threaded stud axially extending from the output shaft and a nut adapted to engage the stud to clamp the blade hub to the handpiece. These collets generally require the use of a separate wrench to turn the clamping nut. U.S. Pat. No. 5,237,884 (Seto) shows a variety of conventional tool-requiring chuck mechanisms in the form of a threaded shaft which is turned to tighten against a clamping plate and saw blade. Since it is desirable to avoid extra tools in a surgical setting, some collets eliminate the need for a separate tool by utilizing a nut (e.g. a wingnut) that can be manipulated without tools. Other collet designs utilize a spring actuated, longitudinally movable clamping head having longitudinally extending locking pins for engagement with corresponding holes in the blade hub. The clamp head in such designs is movable to place the collet into an open position for receiving a blade and into a closed position for clamping the blade between the head and a base surface. Such designs are referred to herein as "wrenchless" designs and are generally preferable to other chuck or collet mechanisms which require the use of separate tools. The terms "chuck" and "collet" are used interchangeably herein.

Yet another wrenchless collet design utilizes a spring actuated clamping plate to frictionally engage a surgical blade. In many cases projecting locking pins extend from a clamping surface to produce a positive engagement with holes in the blade. The blade clamp is momentarily movable by manual pressure directed to compress the spring to an open position for receiving a blade. Release of the manual pressure enables the spring to close the clamp. Such collets are difficult to clean and sterilize due to the need for the spring to be manually held in a compressed position while a blade is inserted or removed or when the collet is cleaned.

U.S. Pat. No. 5,265,343 (Pascaloff), assigned to the assignee hereof, discloses a bi-stable type of wrenchless collet which enables the blade clamp to stay in the open or closed position. The ability to stay open without manual pressure facilitates the loading, cleaning and sterilization of the device. However, this design does not easily lend itself to all types of surgical saws or to miniaturization. Accordingly, there is a need for a bi-stable wrenchless collet adaptable to small surgical instruments.

In the case of oscillating or sagittal surgical saws used with conventional flat blades oscillating in a plane aligned with or parallel to the axis of a pencil-type handpiece, the collet mechanism must be adapted to apply a force to the blade hub in a direction perpendicular to the handpiece axis. For microsurgical procedures such as oral-maxillofacial, ear-nose-throat (ENT) and other procedures in confined areas, the size of the collet must be minimized as much as possible to improve the surgeon visualization of the surgical site. The challenge is to provide as small a collet as possible while providing as much blade holding force as possible while also enabling the collet to stay open for sterilization or loading.

A wrenchless collet chuck in the form of a pushbutton is shown in U.S. Pat. No. 5,383,785 (Brugger) as part of a dental tool. The collet chuck is a hollow cylindrical member with axial slots spaced along the body of the member such that adjacent slots are open at opposite ends of the member in an alternating pattern. The arcuate portions of the cylindrical member between the slots act as clamping elements for holding a tool in axial alignment with the hollow cylinder. A conical control surface is moved by the pushbutton to move the clamping elements radially. This device is, however, not only unsuitable for holding blades perpendicular to the chuck axis but is also unable to maintain an open position without a user having to continually push and hold the button open.

Another representative wrenchless collet is shown in U.K. Patent Application 2,195,274. This device utilizes a plurality of circumferentially arranged locking balls which are biased radially inwardly against an axially aligned tool shaft.

It is an object of this invention to provide a blade collet that does not require a separate tool for its operation.

It is another object of this invention to produce a wrenchless collet for holding a surgical device to a drive mechanism.

It is a further object of this invention to produce a wrenchless blade collet for holding a flat surgical saw blade on an oscillating or sagittal saw.

It is yet another object of this invention to produce a wrenchless blade collet having a minimal size in order to enable its use in microsurgical devices.

It is another object of this invention to provide a blade collet that is easily operated and cleaned.

It is also an object of this invention to provide a wrenchless blade collet which is bi-stable, i.e. having two states such that the collet can be actuated to and stay in either an open position or a closed position by a pushing motion.

It is yet another object of this invention to produce a collet system adapted to securely hold a tissue cutting device to an oscillatory saw.

It is also an object of this invention to produce a wrenchless and adapterless system for securing a surgical blade to a powered handpiece.

It is another object of this invention to produce a system for attaching tissue cutting devices to powered handpieces without the necessity for auxiliary tools.

SUMMARY OF THE INVENTION

These and other objects of this invention are achieved by the preferred embodiment disclosed herein which is a wrenchless collet for holding a cutting device comprising a blade clamp means in the form of a first, axially stationary clamping surface and a second, axially movable clamping surface. The second clamping surface is movable to either an open position, in which it is spaced from the first clamping surface, or a closed position in which it is urged toward the first clamping surface. A clamp holding means is provided for holding the blade clamp in either the open position or the closed position, the clamp holding means comprising a shaft connected to the blade clamp means and a bi-stable biasing means for acting on the shaft to urge it axially either in one direction when the blade clamp is in the closed position or in the other direction when the blade clamp is in the open position. In the preferred embodiment, the bi-stable biasing means comprises a flat V-shaped spring in the form of a unitary member having a central bight portion and a pair of spring legs extending outwardly from the bight portion. The spring is attached to the shaft so that the spring legs normally have a predetermined width greater than the diameter of said shaft. The bight portion is attached to the shaft such that the spring legs lie substantially in a plane parallel to said axis. The shaft and the spring legs slide in a bore which is sized to enable the pair of spring legs to be compressed to a width substantially equal to the diameter of the shaft when the blade clamping means is in the open position. A spring leg expansion means is provided for enabling the pair of spring legs to return toward their normal, unbiased state, when the blade clamp means is in the closed position.

The invention disclosed herein is also in the method of selectively attaching a cutting device to a surgical handpiece comprising the steps of providing a wrenchless collet having a first clamping surface member and a second clamping surface member, the members relatively movable between a closed position wherein they are aligned such that a cutting device may be held between the members and an open position wherein they are spaced and a cutting device may be inserted or removed therefrom. A clamp holding means is provided to hold the wrenchless collet either open or closed. A user accessible means is secured to the first clamping surface member to push it either toward or away from the second clamping surface member. The wrenchless collet is selectively opened by pushing the user accessible means in a first direction to move the first clamping surface member axially in one direction or selectively closed by pushing the user accessible means in a second direction to move the first clamping surface member axially in an opposite direction.

DESCRIPTION OF THE PREFERRED EMBODIMENT

As shown in FIGS. 1 through 6, a wrenchless blade collet 10 constructed in accordance with the principles of this invention is mounted to the distal end of a powered surgical handpiece 12 such as an oscillating saw or sagittal saw. Collet 10 is intended for use with a flat surgical saw blade 14 and is designed to stay in either a closed position (best seen in FIG. 1) in which it will hold blade 14 so that it may be driven in an operative manner by handpiece 12 (i.e. in either a sagittal or oscillating mode), or in an open position (best seen in FIG. 6) to enable the blade to be assembled with or removed from the collet, or to enable the collet to be sterilized and cleaned.

Figure 1:
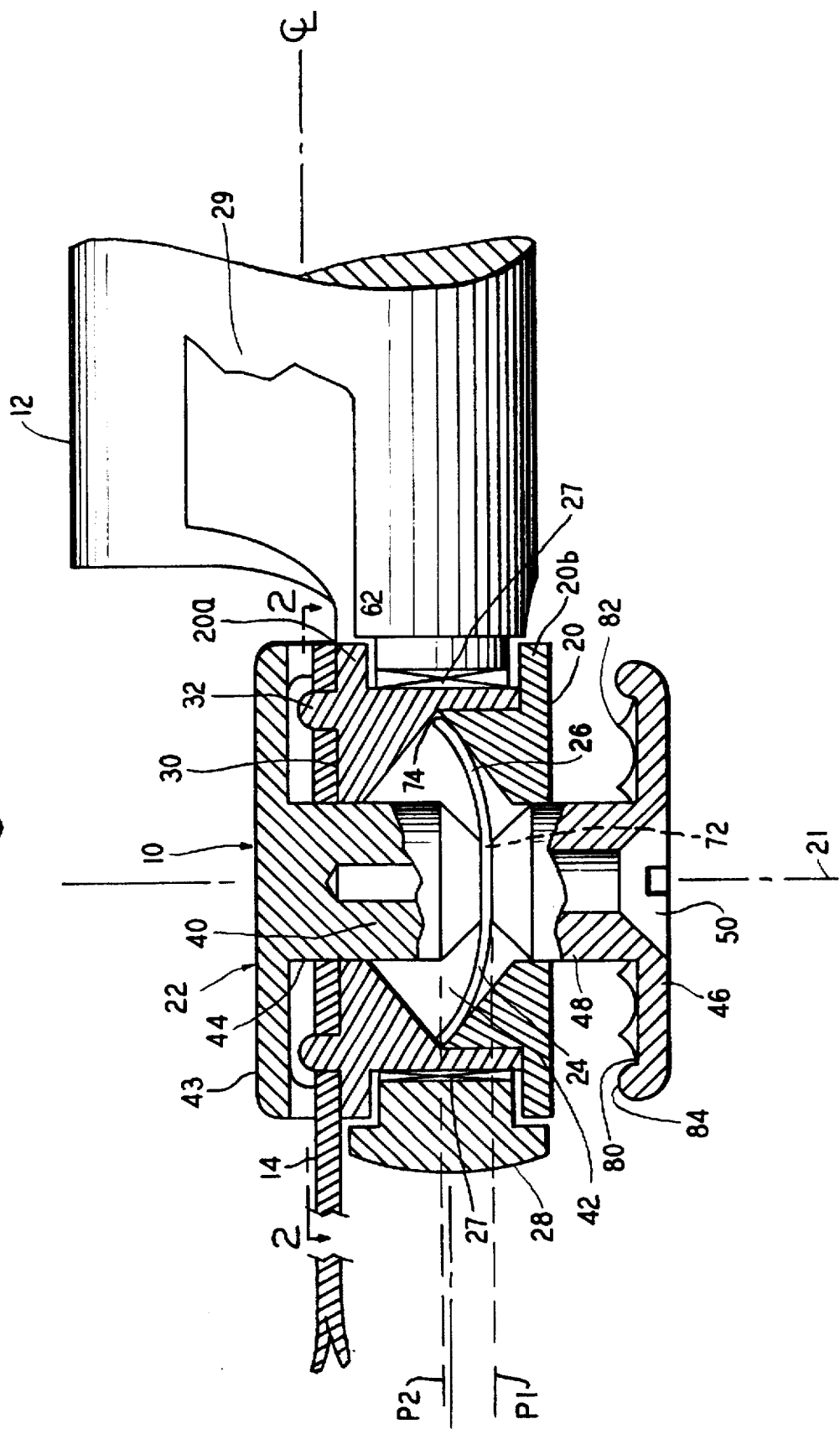
FIG. 1 is a side elevation view, in cross-section, of the distal end of a sagittal saw showing one embodiment of the invention in a closed position.
Figure 2:
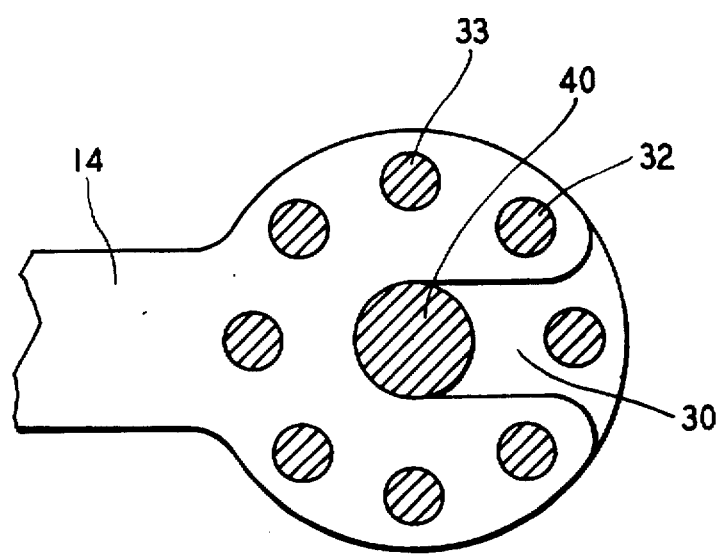
FIG. 2 is a cross-sectional view of FIG. 1 taken along the line 2—2.
Figure 3:
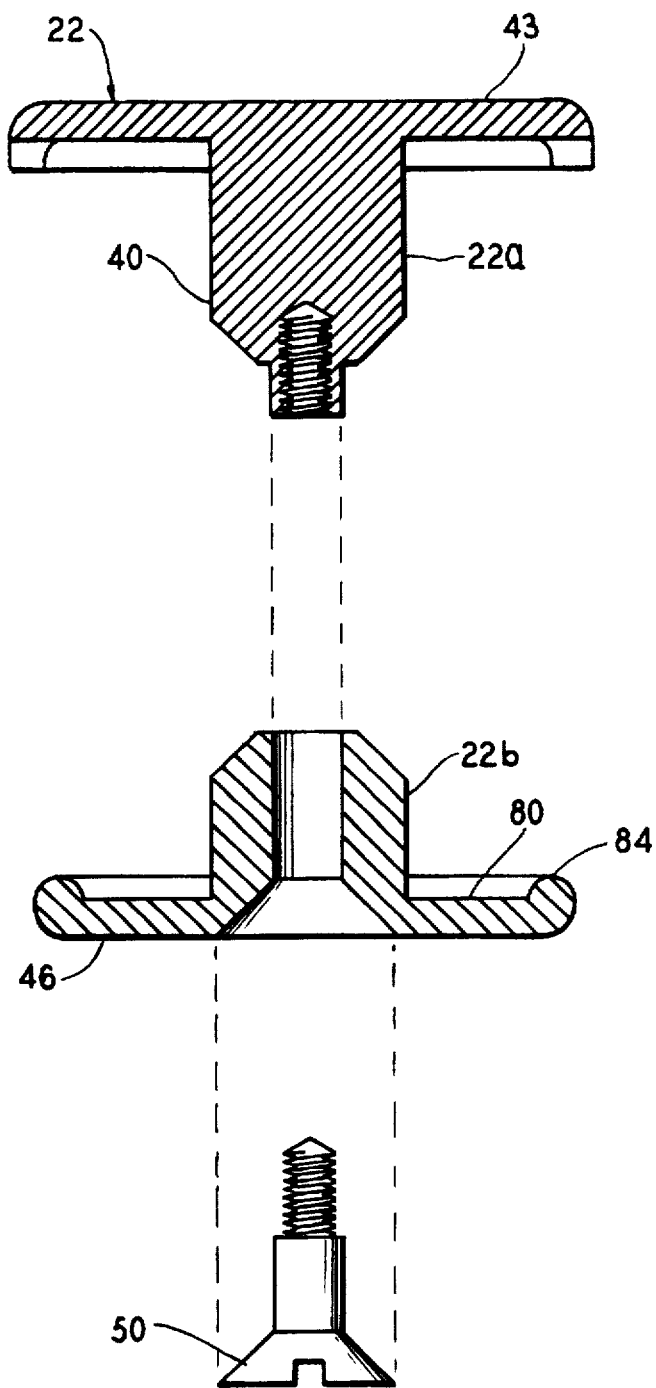
FIG. 3 is an exploded view of a component part of the embodiment of the invention shown in FIG. 1.
Figure 4:
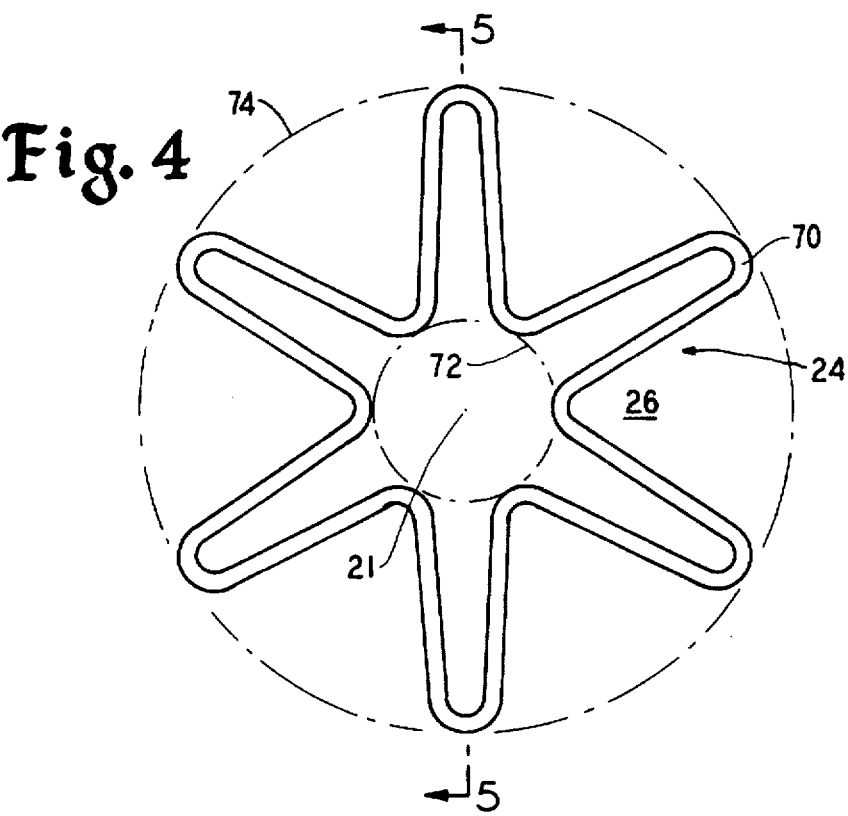
FIG. 4 is a plan view of another component part of the embodiment of the invention shown in FIG. 1.
Figure 5:
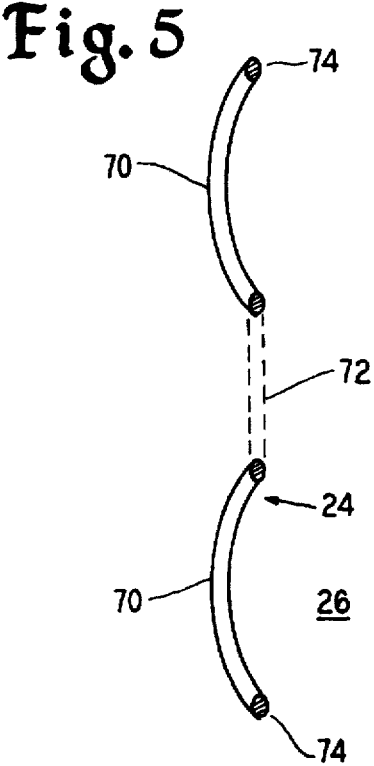
FIG. 5 is a cross-sectional view of FIG. 4 taken along the line 5—5.
Figure 6:
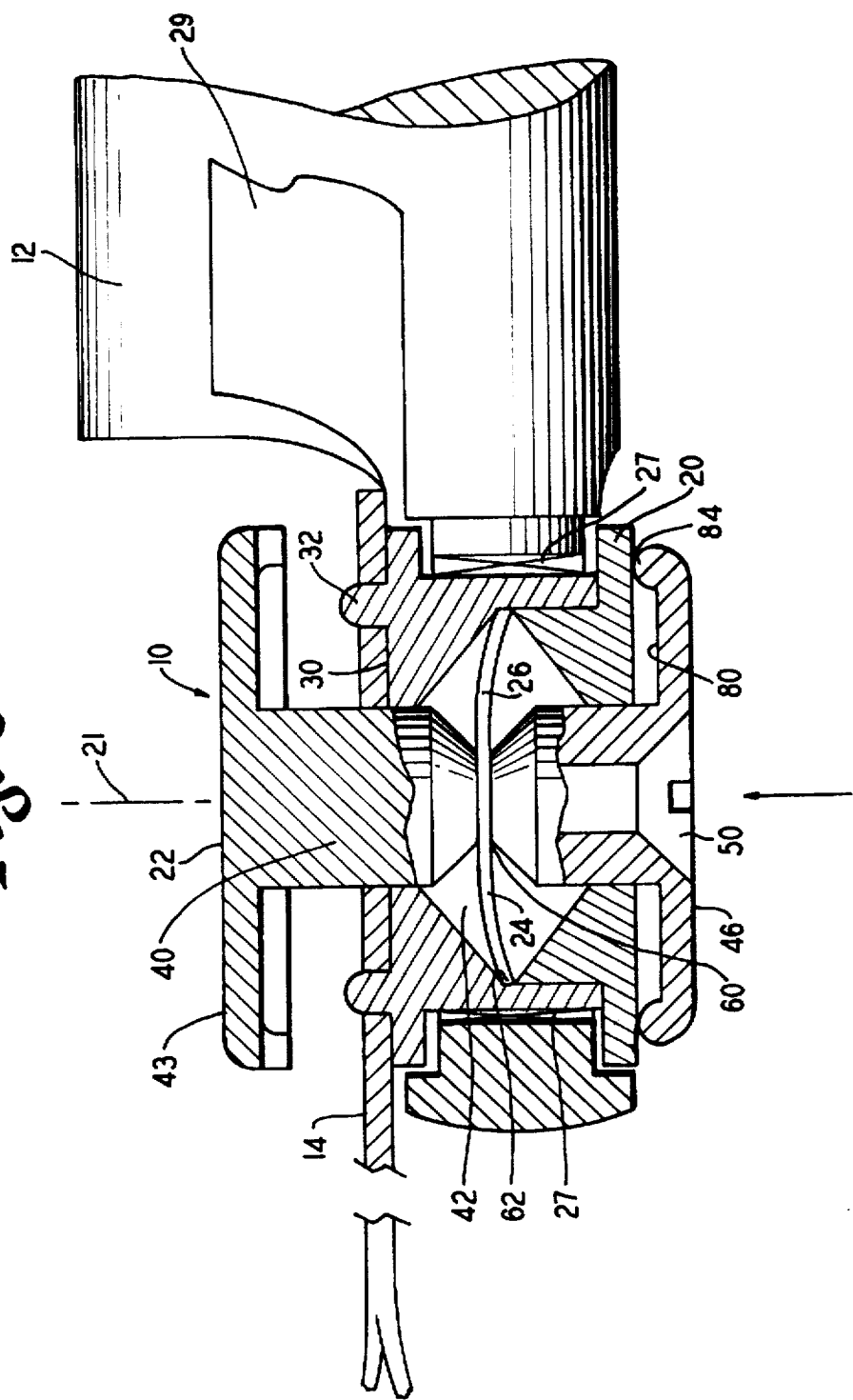
FIG. 6 is a view of FIG. 1 showing the embodiment in an open position.

Collet 10 comprises a housing 20 having an axis 21, a blade clamp 22 and a bi-stable clamp operating or holding mechanism 24 which, in the first embodiment shown in FIGS. 1–6, is a toroidal, overcenter biasing spring 26, best seen in plan view in FIG. 4. The preferred embodiment of toroidal spring 26 comprises a single wire formed into a star-like shape having a plurality of lobes 70, the tips of which define an inner circular periphery 72 and an outer circular periphery 74. Depending on the chosen design, both circular peripheries and the spring body may be concentric and co-planar when the spring is in its neutral state or the spring body between these peripheries may be outside this plane (as diagrammatically shown in FIG. 5). Nevertheless, the spring is intended to exert a force in each of two states, i.e. opened and closed, and in each of these states the collet will maintain the set position. The term bi-stable is used to indicate that the spring is able to hold the collet either open or closed. It is not intended to mean the spring is stable in any position without cooperative action with its housing. Thus, when placed in one of its biased states and viewed from the side (as shown in FIG. 1) the inner circular periphery 72 is situated in one plane P1 perpendicular to axis 21 while the outer circular periphery 74 is situated in another, parallel plane P2. A similar, but reversed arrangement is shown in FIG. 6 when the spring is in its other biased state.

Housing 20 comprises upper and lower sections 20a and 20b, respectively, situated in a bearing 27 at distal end 28 of handpiece 12, and is connected (by means not shown) to a driver means 29 which imparts to housing 20 (and thereby to blade 14) the appropriate oscillating drive motion about axis 21. As best seen in FIGS. 1 and 2, housing 20 has a top clamping surface 30 provided with a plurality of annularly arranged projecting pins 32 intended to be received within corresponding apertures 33 in the hub or proximal end of blade 14. The pins and apertures may be circular in cross-section as shown, conical, rectilinear as shown in U.S. Pat. Des. 362,065 assigned to the assignee hereof, or may have any other suitable cross-section.

Bi-stable clamp operating mechanism 24 comprises a shaft 40 having ends 44 and 48, the shaft extending through bore 42 of housing 20 to provide a pushing member at each end. The shaft is provided with an enlarged, transverse clamping head 43 at end 44 and an enlarged transverse pushbutton 46 at the other end 48. In the preferred embodiment, head 43 is at all times parallel to surface 30 although it will be understood that some other relationship (e.g. conical interface, contoured, etc.) may also be used within the scope of this invention. As will be understood below, both the clamping head and the pushbutton serve as pushing members to alternately push shaft 40 in one axial direction or the other. In the preferred embodiment, clamping head 43 is axially movable relative to the shaft axis while surface 30 is axially stationary. The shaft and bore may be keyed or provided with non-circular cross-sections to keep head 43 from rotating relative to surface 30. Since pushbutton 46 is enlarged and attached to end 48, it prevents travel of shaft 40 beyond a predetermined point and makes it easy for a user to push on shaft 40 in an activating direction aligned with axis 21 to open the blade clamp. The large sizes of the clamping head and the pushbutton facilitate the use of the device by providing a tactile indication to enable a user to merely push the shaft at one end or the other.

Shaft 40 is provided with an inner, annular V-shaped recess in the form of groove 60 interposed between ends 44 and 48 and intended to operate with bi-stable operating mechanism 24 by receiving the inner circular periphery 72 of toroidal spring 26. As shown in FIG. 3, the preferred embodiment of shaft 40 is formed of two cylindrical extensions 22a and 22b joined by screw 50 and defining groove 60 at their juncture. Similarly, housing 20 is provided with an outer, annular groove 62 intended to receive the outer circular periphery 74 of toroidal spring 26. The interior 42 between grooves 60 and 62 serves as an expansion chamber for the spring and its shape is somewhat dependent upon the characteristics of spring 26. The diameters of grooves 60 and 62 are chosen such that spring 26 can maintain a biasing force on groove 60 and, therefore, on shaft 40. This force must be sufficient to bias shaft 40 downwardly in a closed position as shown in FIG. 1 to thereby urge clamping member 43 towards clamping surface 30 to thereby retain it and blade 14 adjacent posts 32 and surface 30. Similarly, when the clamp is opened, the force must be enough to hold it open as shown in FIG. 6. The interaction of the spring and its associated structures serves to selectively transfer and direct the spring force to the shaft and ultimately to the clamping surfaces. It will be understood that as transverse pushbutton end 46 is pushed upwardly relative to FIG. 1 to the position shown in FIG. 6, the force of toroidal spring 26 will be overcome and it will be compressed over its neutral "center" position. At that point, the spring force is redirected to place the spring into the position shown in FIG. 6 in which it will bias shaft 40 upwardly to keep clamping surface 43 spaced from clamping surface 30, thereby holding blade clamp 22 in an open position.

The inner surface 80 of pushbutton 46 may be provided with a roughened surface such as a plurality of projections 82 which facilitate the sterilization of collet 10 in the open position. The projections are only shown by way of example in FIG. 1 while FIGS. 3 and 5 show surface 80 as being flat, albeit recessed from an annular lip 84 which may have radially extending channels therethrough (not shown).

Figure 7:
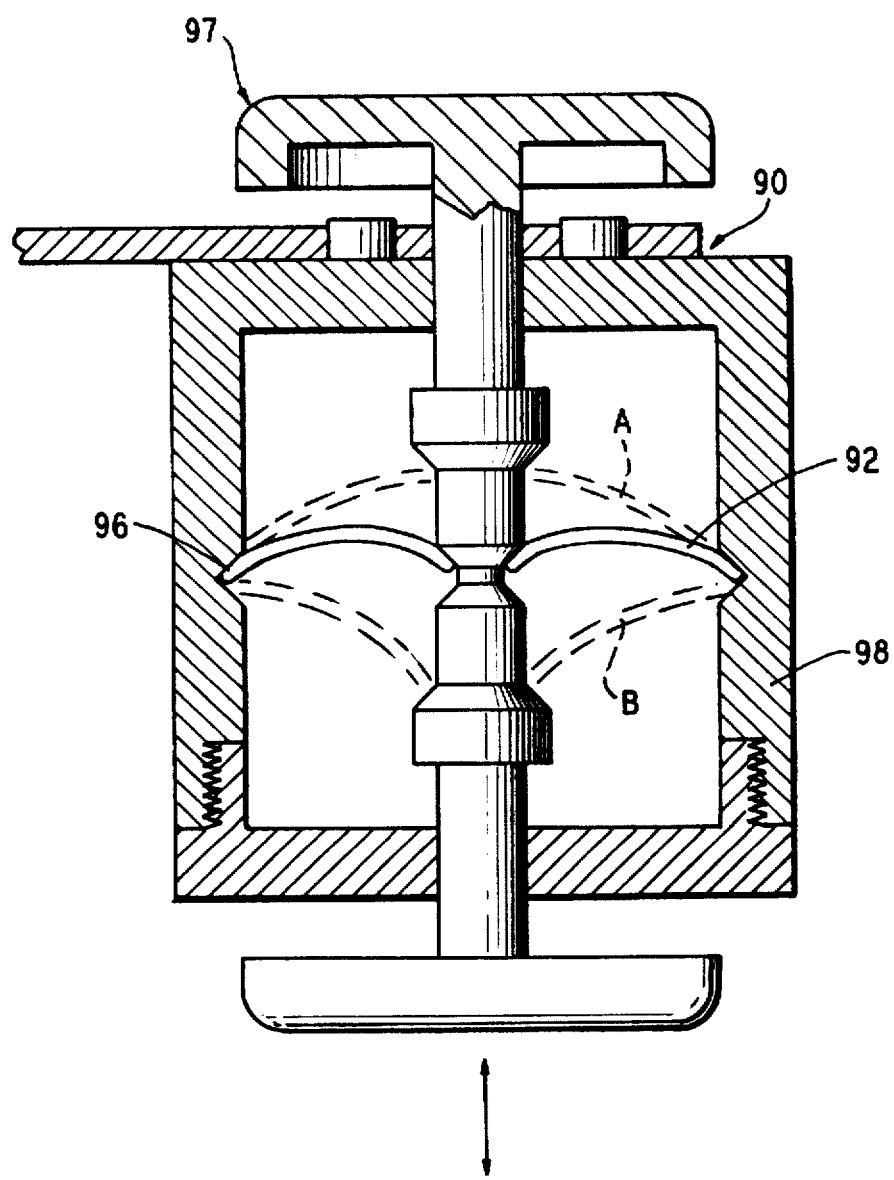
FIG. 7 is a diagrammatic view in cross-section of another alternate embodiment of the invention.
Figure 8:
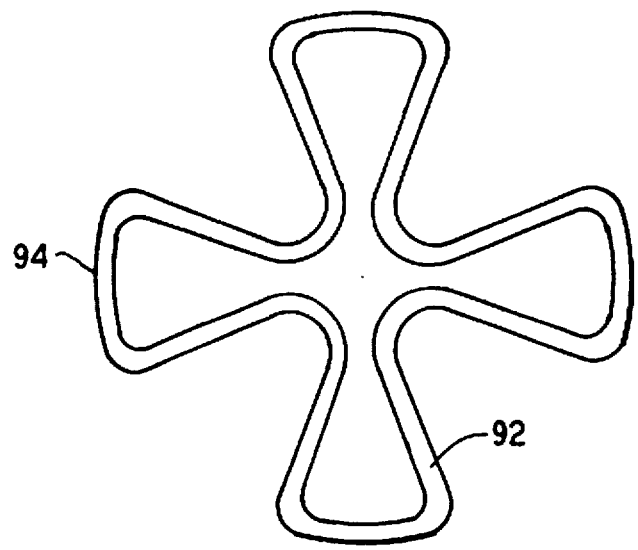
FIG. 8 is a plan view of a component part of FIG. 7.
Figure 9:
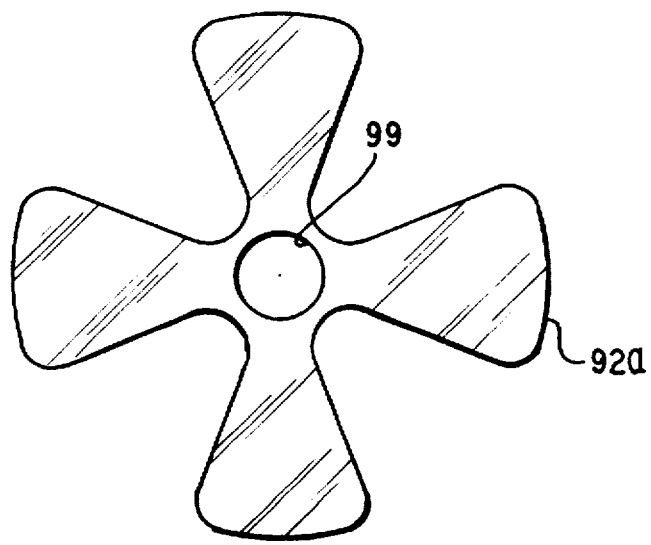
FIG. 9 is an alternate embodiment of the part shown in FIG. 8.
Figure 10:
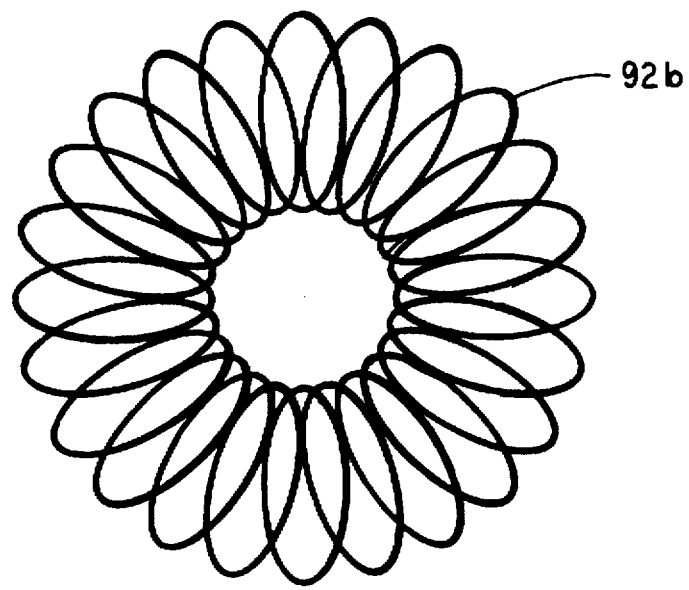
FIG. 10 is another alternate embodiment of the part shown in FIG. 8.

Another simplified variation of the previous embodiment is shown in FIG. 7 as collet 90 employing a toroidal, overcenter spring 92 having two stable states, best seen in phantom in FIG. 7. Collet 90 differs from collet 10 in that it is housed in a unitary housing and the junction between the shaft and spring is assembled differently. Spring 92 is a formed wire similar in function to spring 26 and having similar inner and outer circular peripheries, but with a different profile in plan view, as best seen in FIG. 8. The radially outward arcuate segments 94 enable use of complementarily shaped spaced arcuate apertures (not shown) within the groove 96 in the wall of housing 98 rather than a continuous groove similar to groove 62 of FIG. 1. An alternate embodiment of spring 92, shown in FIG. 9 as spring 92a, is formed of a unitary piece of material having a central bore 99 which defines the inner periphery. FIG. 10 shows another spring 92b formed of a multi-coiled, single piece of wire. In operation, the clamp head 97 of collet 90 is held open, when spring 92 is biased to one of its bi-stable states A, and closed when the spring is in the other of its bi-stable states B. Both states are shown in phantom while an unstable, transition position of spring 92 is shown in full lines. The shape of the spring body in these views is merely intended to show that the spring shape changes as the shaft is moved, and is not intended to be an exact depiction of spring shape.

Figure 11:
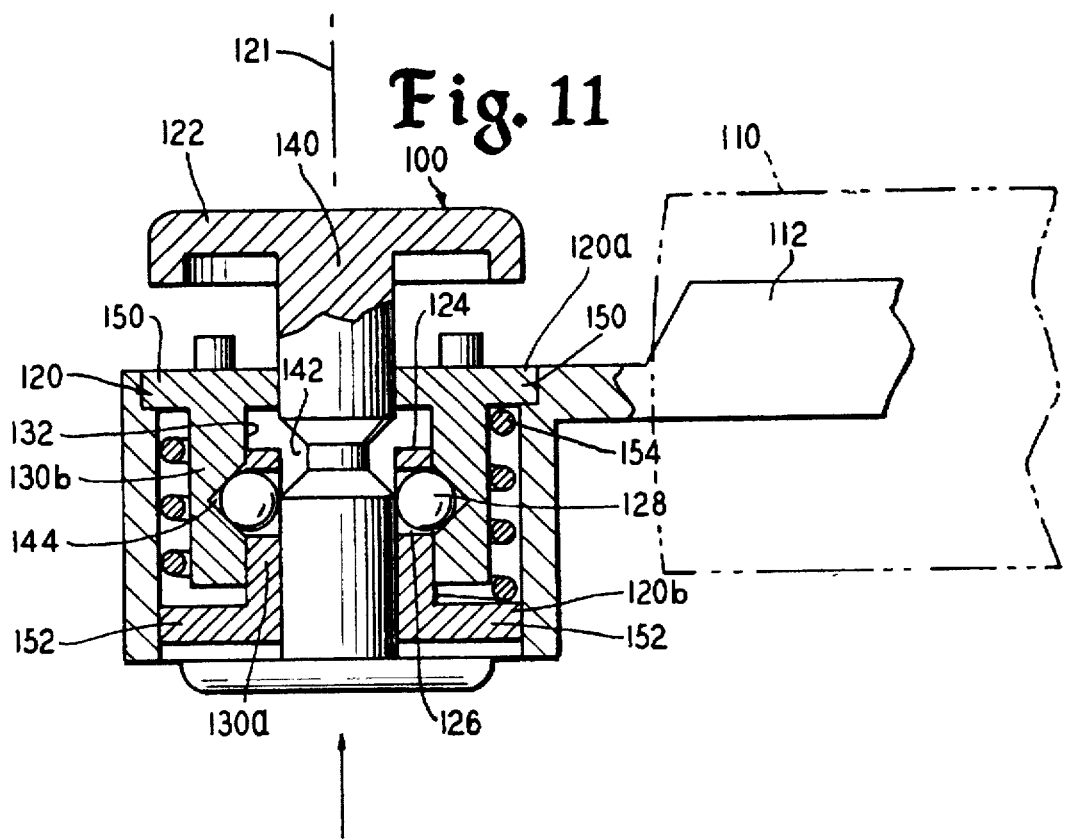
FIG. 11 is a side elevation view, in cross-section, of an alternate embodiment of the invention in an open position.
Figure 12:
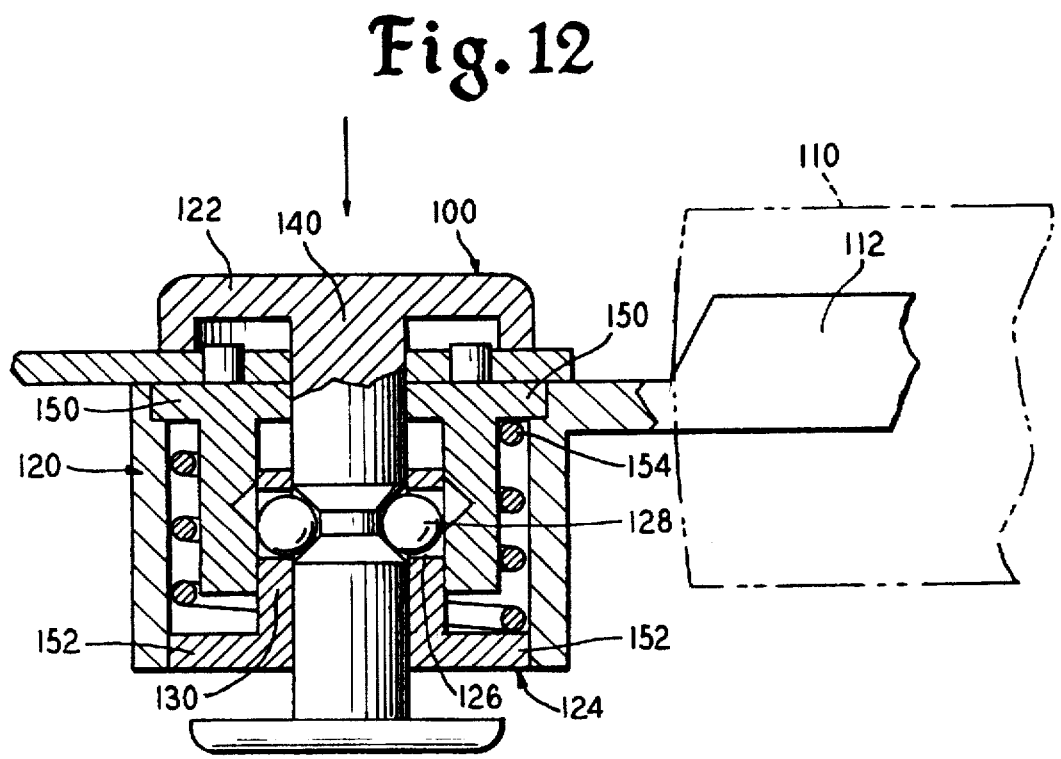
FIG. 12 is a view of FIG. 11 showing the embodiment in a closed position.
Figure 13:
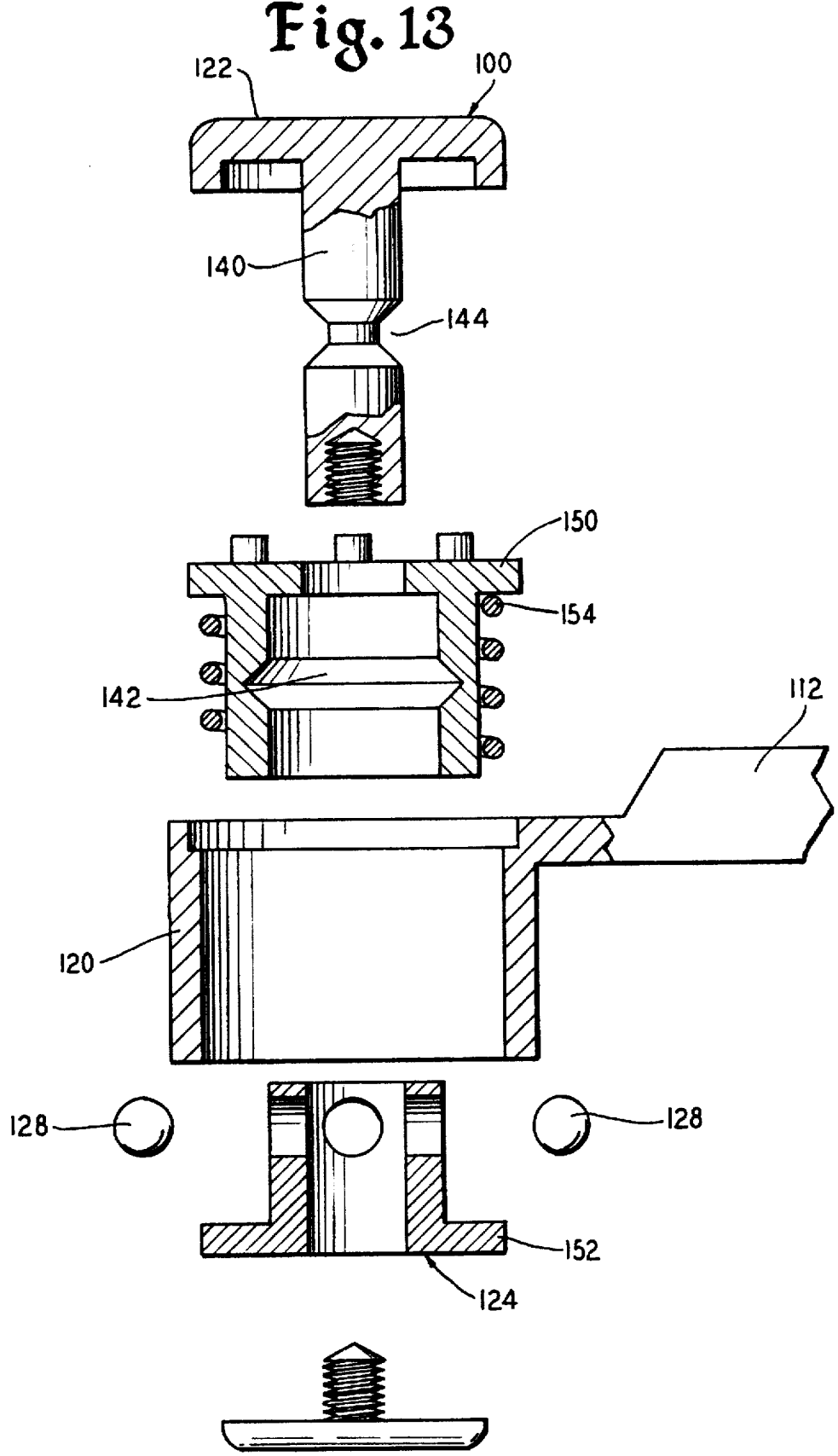
FIG. 13 is an exploded view of FIG. 11.

As shown in FIGS. 11, 12 and 13, an alternate embodiment of the invention comprises a wrenchless collet 100 attached to the distal end of a surgical handpiece 110 having an oscillating drive member 112. Collet 100 is similar in function to collet 10 and differs in the embodiment of the invention by which the blade clamp is held in either the open or closed position.

Collet 100 comprises a housing 120 having an axis 121, a bi-stable blade clamp 122 and a dual-action, rolling member retaining mechanism 124. Housing 120 has upper and lower portions 120a and 120b, respectively, each of which has longitudinally extending cylindrical walls 130a and 130b, respectively. Upper housing section 120a is provided with a flange 150 and lower housing section 120b is provided with a flange 152, both flanges serving to retain a spring 154 therebetween. In the embodiment shown, rolling member retaining mechanism 124 utilizes spherical members rather than cylindrical members and comprises a cylindrical ball carrier 126 formed integrally with lower housing 120b, surrounding shaft 140 and retaining a plurality of circumferentially spaced locking balls 128. The radial thickness of the cylindrical wall 130a of ball carrier 126 is substantially equal to the size of the annular gap between shaft 140 and the cylindrical wall 130b of upper housing portion 120a. Shaft 140 has a first annular groove 142 into which balls 128 are partially received when the blade clamp is in its closed position (FIG. 12) and wall 130b has a second annular groove 144 into which balls 128 are partially received when the blade clamp is in its open position (as best seen in FIG. 11). It will be noted that annular groove 142 has two oppositely facing, axially spaced tapered side surfaces such that any axial force imparted by balls 128 to the tapered surfaces will move the shaft axially. Groove 144 also has two oppositely facing tapered side surfaces to receive the balls 128 and transfer compressive force from the housing to the shaft. It will be noted that lower housing portion 120b travels a predetermined axial distance between the open and closed positions in order to accommodate the rolling motion of balls 128. The diameter of each of the locking balls 128 is substantially equal to (or only slightly greater than) the size of the spaces within which the balls are intended to move. Thus, at one extreme of axial motion as shown in FIG. 12 the diameter of the locking balls is equal to the distance between the radially innermost side of wall 130b and the floor of annular groove 142. As the lower tapered surface of groove 142 pushes the ball upwardly in the process of moving collet 100 from the closed position to the open position shown in FIG. 11, the ball rolls within the space between the radially innermost side of wall 130b and the floor of annular groove 142 until it clears the lower edge of annular groove 144. At this point, the ball naturally rolls into this groove as the shaft is moved further into the open position until the locking balls are captured between the floor of annular groove 144 and the radially outermost surface of shaft 140 as shown in FIG. 11. The frictional engagement at this point maintains the collet in an open position.

The grooves 142 and 144 may be replaced by one or more coplanar recesses (not shown) which are arranged angularly about axis 121 in order to be aligned to receive a locking ball associated therewith.

Figure 14:
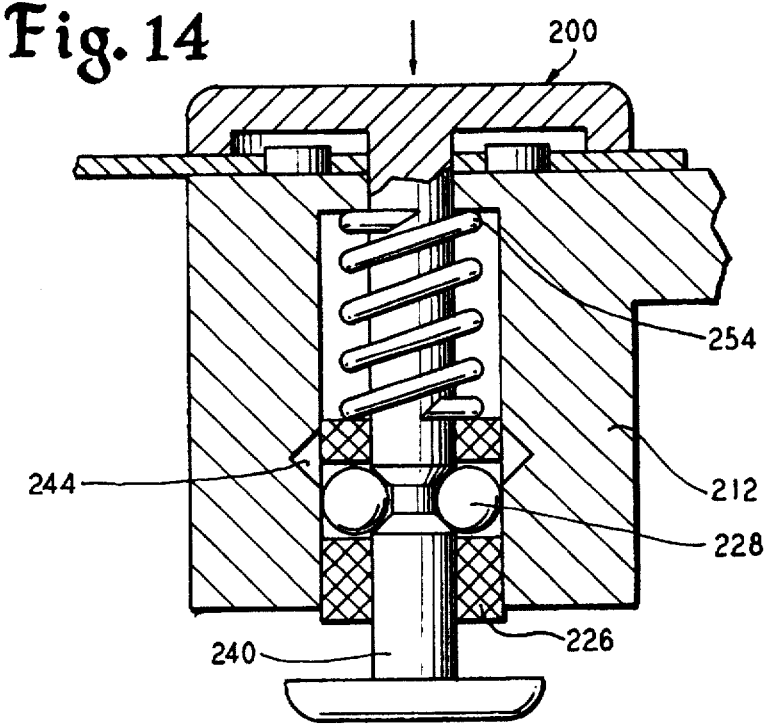
FIG. 14 is a side elevation view in cross-section of another alternate embodiment of the invention in a closed position.
Figure 15:
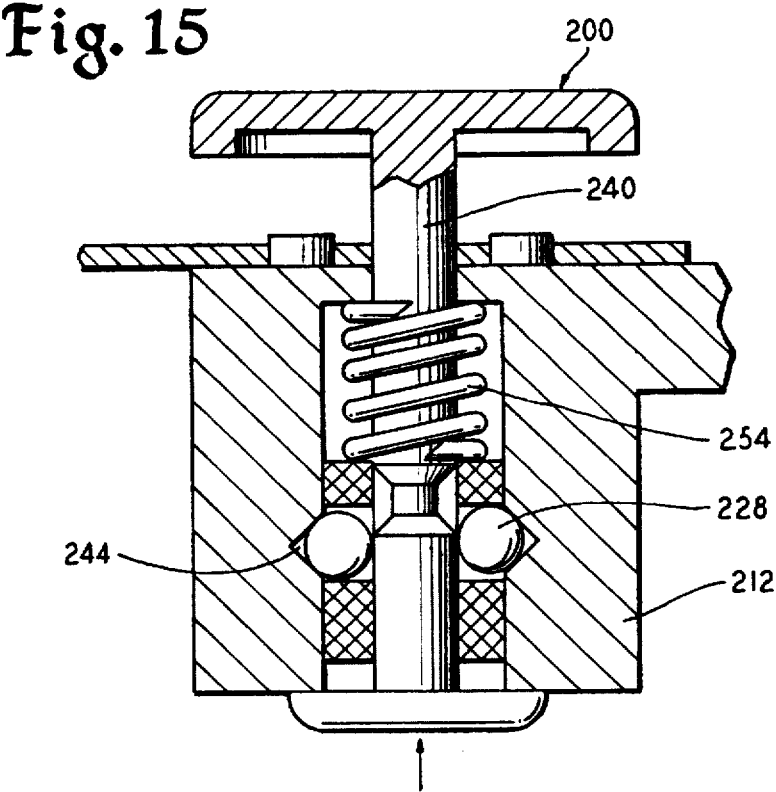
FIG. 15 is a view of FIG. 14 in an open position.

Another embodiment of the invention is shown in FIGS. 14 and 15 as collet 200 which operates similarly to collet 100 except that the spring 254 is located adjacent the shaft. Shaft 240 has an intermediate groove 242 which receives balls 228 in the closed position. Ball carrier 226 holds balls 228 and moves within the gap between shaft 240 and body 212. The latter is provided with groove 244 to receive balls 228 in the open position.

Figure 16:
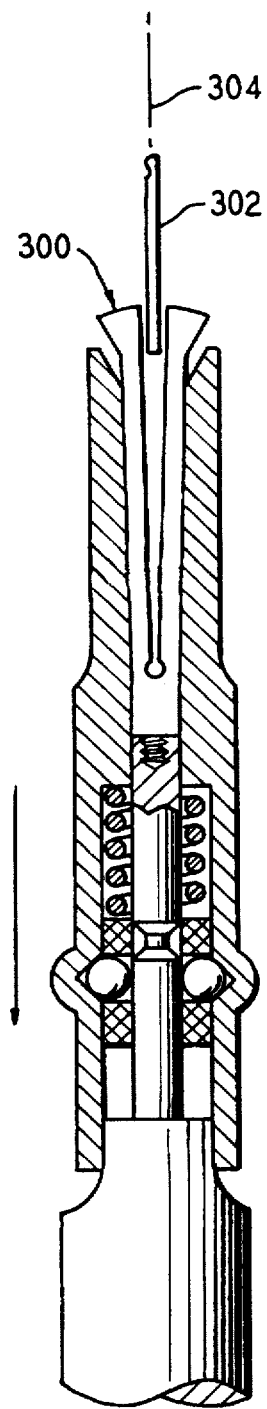
FIG. 16 is a diagrammatic view in cross-section of another alternate embodiment of the invention in an open position.
Figure 17:
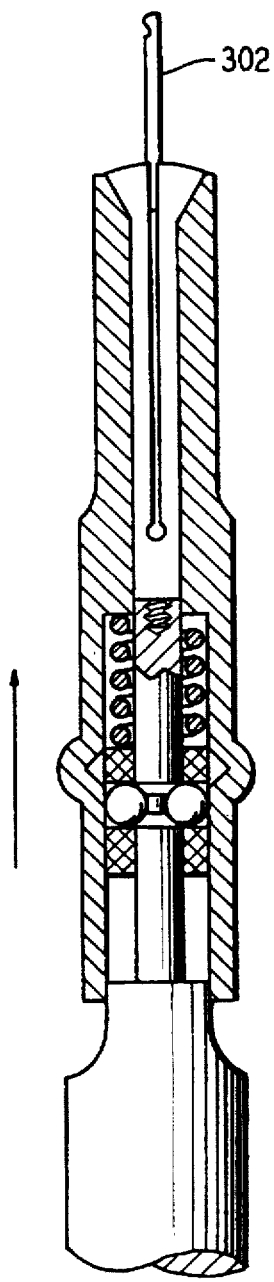
FIG. 17 is a view of FIG. 16 in a closed position.

Another embodiment of the invention is shown in FIG. 16 as collet 300 shown in an embodiment adapted to axially retain an elongated shaft 302 such as a drill bit or other axially elongated tool. This embodiment operates similarly to that shown in FIGS. 14 and 15. The clamping mechanism of collet 300 provides a tool retention force in a direction perpendicular to the axis 304 of the collet shaft in order to frictionally engage tool shaft 302 in axial alignment with the collet shaft.

Figure 18:
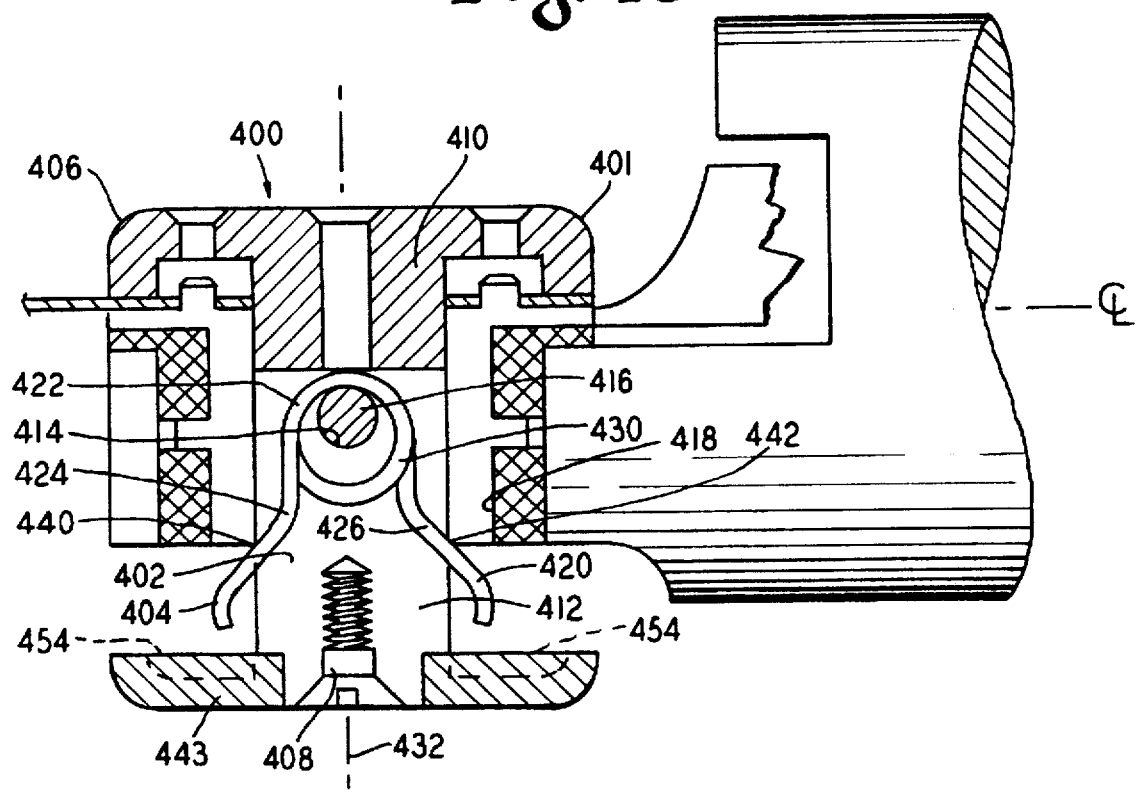
FIG. 18 is a side elevation view in cross-section of another alternate embodiment of the invention in a closed position.
Figure 21:
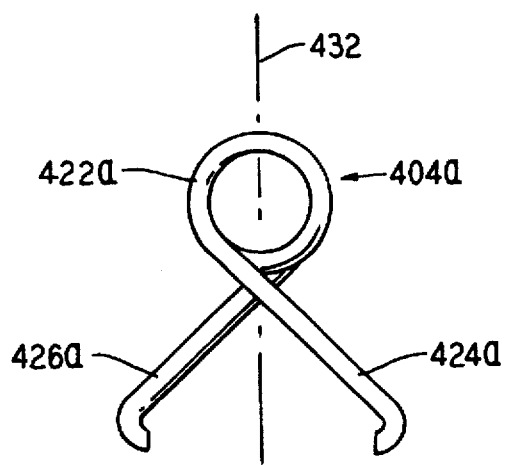
FIG. 21 is an alternate embodiment of a spring used in the embodiment shown in FIG. 18.

Another embodiment of the invention is shown in FIGS. 18 through 21 as collet 400 comprising blade clamp 401, shaft 402 and spring 404. Other components are similar to previous embodiments and need not be separately explained here. Shaft 402 has cylindrical body 410, a clamp head 406 at one end thereof and a screw-receiving bore 408 at the other end. The end of shaft 402 adjacent bore 408 is provided with a transverse axial slot 412 and the closed end of the slot is provided with a bore 414 perpendicular to the slot. The cross-section of body 410 is shaped and keyed to fit in bore 418 within which the shaft moves without rotation. Spring 404 comprises a flat, pre-formed spring member 420 having a central bight portion 422 from which spring legs 424 and 426 extend. The spring legs extend in generally the same direction relative to bight portion 422 so spring 404 has a general "V" shape. A simple yet effective spring 404 may be formed from a length of wire shaped to have a bight portion 422 in the form of a simple bend or with one or more coiled loops 430 as shown. Spring legs 424 and 426 can remain on the same side of the spring axis 432 from which they originate (as best seen in FIG. 18). Alternatively, an embodiment such as spring 404a could be produced such that spring legs 424a and 426a extend from bight portion 422a and cross the axis 432 as best seen in FIG. 21. Bore 414 is adapted to receive pin 416 which retains spring 404 within transverse slot 412.

Figure 19:
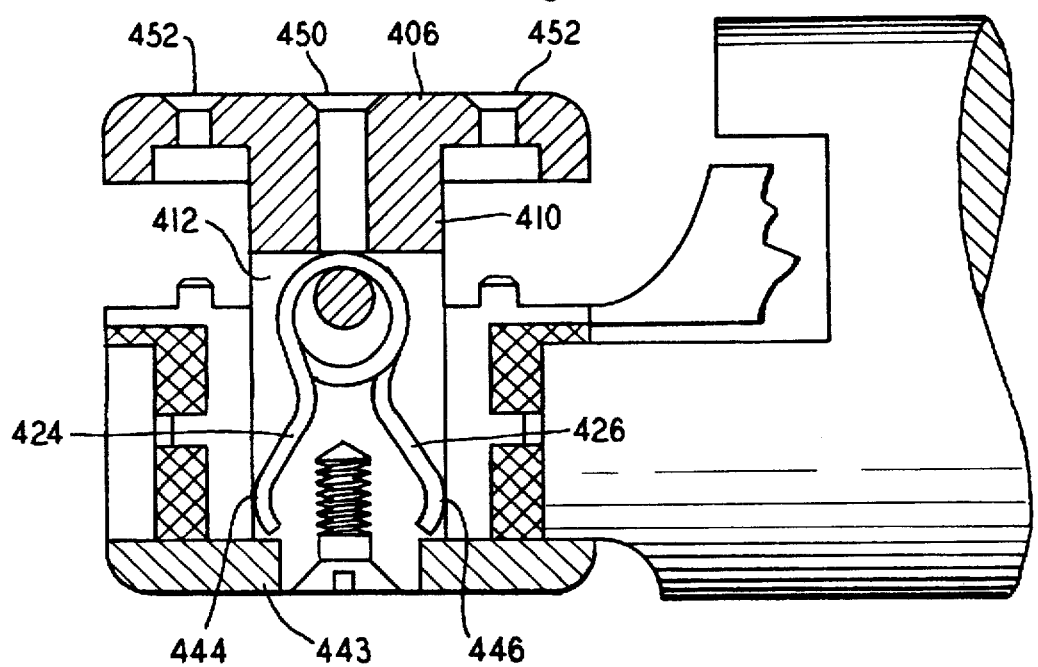
FIG. 19 is a view of the embodiment of FIG. 18 in an open position.
Figure 20:
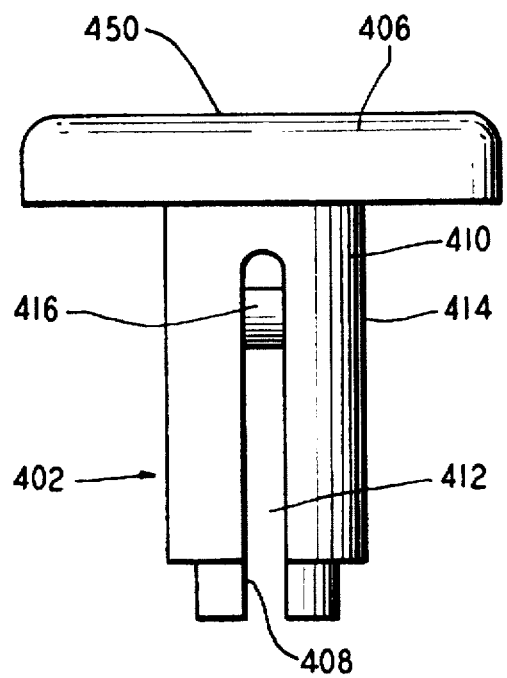
FIG. 20 is an elevation view of a component of FIG. 18.

While spring legs 424/426 and 424a/426a are normally in a "V" configuration as best seen in FIGS. 18 and 19, the curvature of the legs may vary from some curve as shown in FIG. 18 to fairly straight as shown in FIG. 21. The curvature of the spring legs affects the degree of travel of shaft 402 and the clamping force. Starting from the closed position shown in FIG. 18, it will be understood that as the pushbutton end of the shaft 402 is pushed upwardly, the inside edges 440 and 442 of the housing (actually opposite sides of the bottom circular edge of bore 418) push the spring legs inwardly such that when pushbutton 443 abuts the bottom end of the housing, the radially outermost surfaces 444 and 446 of spring legs 424 and 426 contact the inside wall of bore 418 as best seen in FIG. 19. The frictional engagement at these points holds clamp head 406 open and the curvature imparted to legs 424/426 helps provide this force. Similarly, starting from an open position as clamp head 406 is pushed downwardly, the contact points 444 and 446 eventually clear edges 440 and 442 and the natural spring force of spring 404 will assist in its further downward motion. The collet reaches its closed position before the spring legs are able to reach their unbiased state so the spring can continue to apply a clamping force. The curvature of the legs between points 444/446 and the central bight portion will affect the speed of the spring-assisted downward motion as well as the ultimate clamping force once the clamp head is closed.

Various channels and cut-outs may be provided to facilitate cleaning and sterilization. For example, an axial channel 450 may be provided in the clamp head to enable communication between slot 412 and the outside surface of clamp head 406. Similarly, a plurality of annularly arranged throughbores 452 may be situated within clamp head 406 above each pin location. Also, radial cut-outs 454 may be provided to access the interior.

Figure 22:
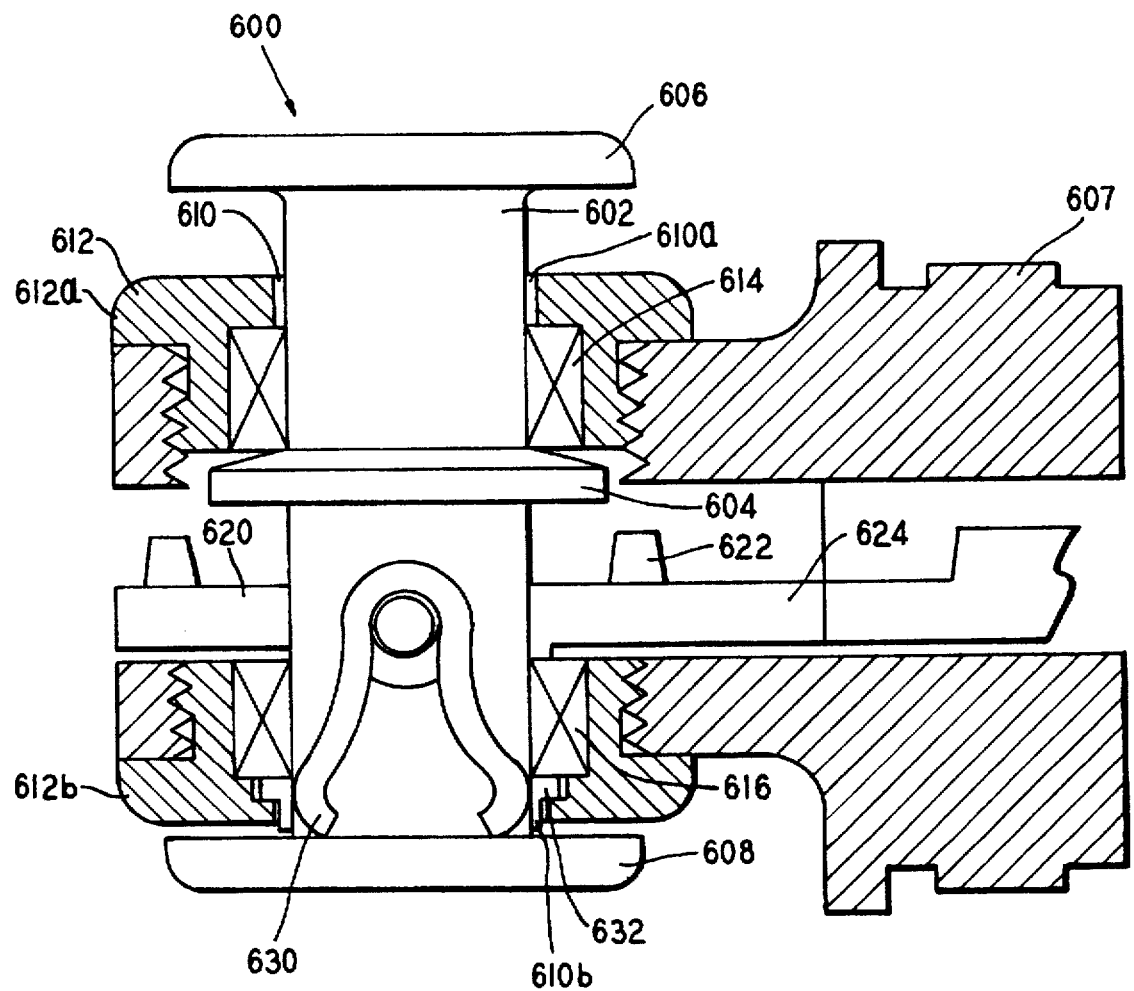
FIG. 22 is a side elevation view in cross-section of another alternate embodiment of the invention in an open position.

Another alternate embodiment of the invention is shown in FIG. 22 as collet 600 which incorporates a modified shaft 602 having an intermediate clamp head 604 interposed between shaft ends 606 and 608. Shaft 602 is attached to a sagittal saw 607 and is adapted to reciprocate within bore 610 of housing 612 although both of these elements are split into upper and lower portions 610a/610b and 612a/612b, respectively. While previous embodiments were one-sided, single bearing designs, this arrangement enables each bore portion 610a and 610b to be provided with its own bearing 614 and 616, respectively, to more efficiently dissipate heat where high cyclical speeds are required. Clamp head 604 is shown in FIG. 22 in an open position spaced above clamp surface 620 and pins 622 on drive element 624. Spring 630 is similar to spring 404 and operates adjacent a hardened thrust collar or bushing 632 secured to rim of bore 610b adjacent the spring legs in order to enhance performance of the invention. Spring 630 acts like the previously described springs of similar design to place and hold clamping head 604 in a closed position (not shown) to hold a blade (not shown) between head 604 and clamping surface 620.

Figure 23:
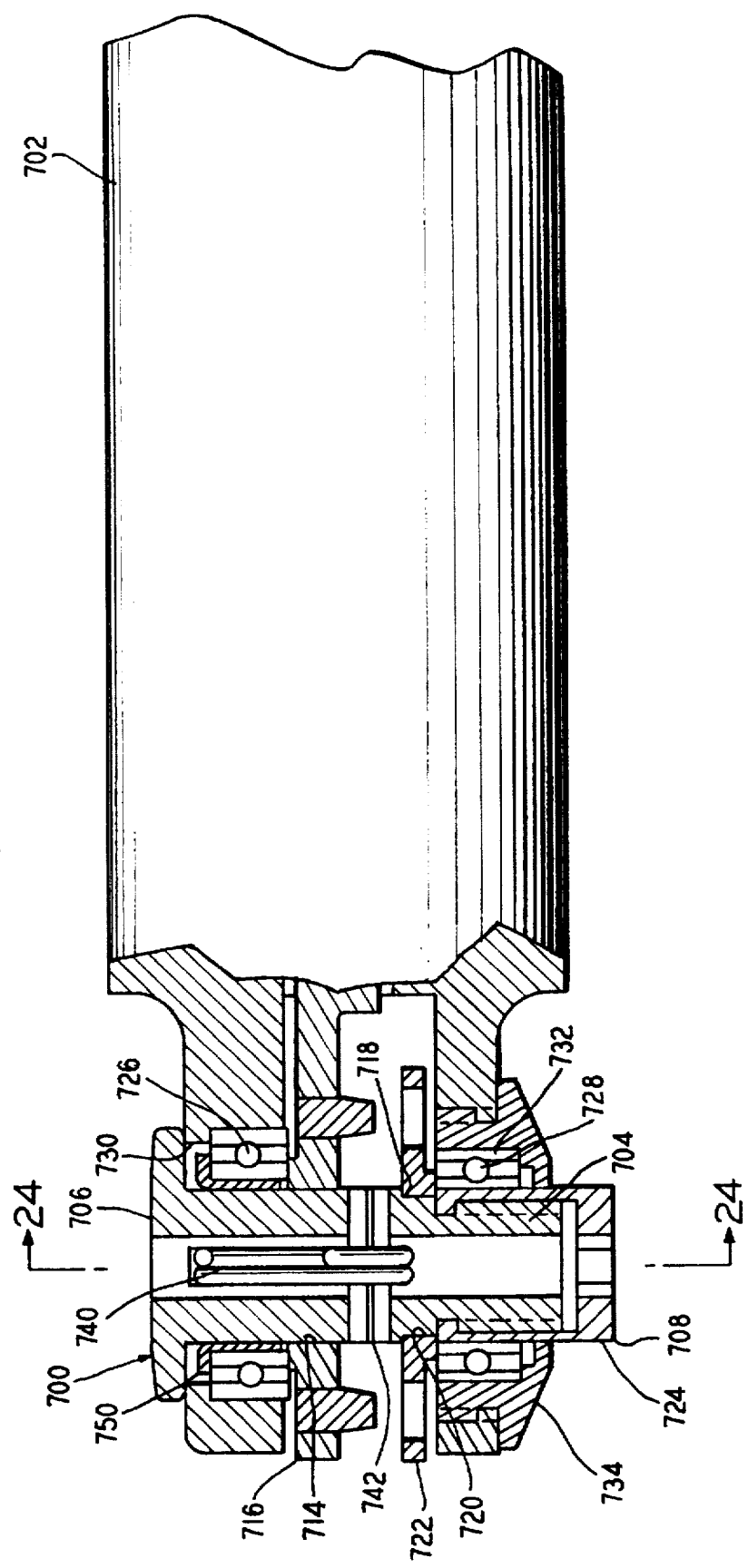
FIG. 23 is a side elevation view in cross-section of another alternate embodiment of the invention in an open position.
Figure 24:
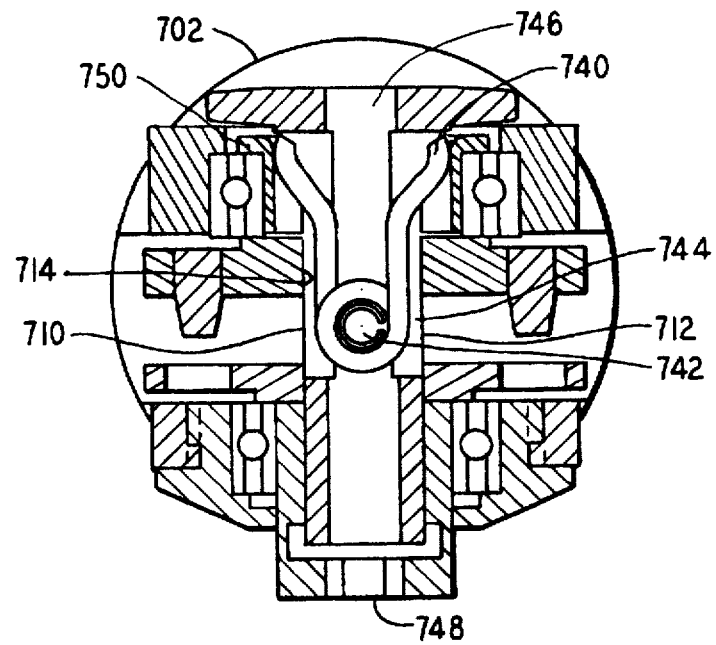
FIG. 24 is a cross-section of FIG. 23 taken along the line 24—24.
Figure 25:
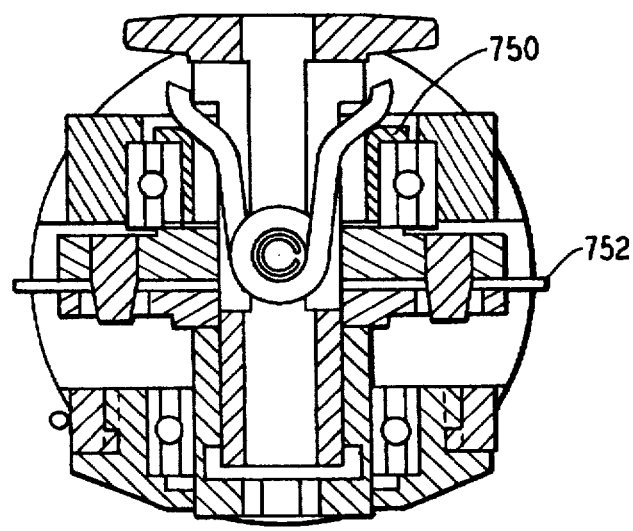
FIG. 25 is a view of FIG. 24 showing the invention in a closed position with a blade.

A variation of this embodiment is shown in FIGS. 23-25 as collet 700 attached to sagittal saw 702. The structure of collet 700 is similar to that of collet 600 with slight variations. For example, the housing within which collet 700 is situated is a pair of integral extensions of the saw body. Collet 700 comprises a shaft 704 having an enlarged end 706 and a smaller other end 708 to provide a tactile indication of which end to push to open or close the collet. In the embodiment shown, pushing the large end opens the collet although the sizes of the ends could be reversed. Similar tactile indicators may clearly be used with all of the other embodiments disclosed herein. Shaft 704 is cylindrical with a generally circular cross-section which has two flattened sides 710 and 712, best seen in FIG. 24, which enable shaft 702 to slide without rotating within a generally rectangular aperture 714 in driver 716. A shoulder 718 is provided to receive a similar rectangular aperture 720 in plate 722 and a threaded keeper 724 is used to secure plate 722 adjacent shoulder 718 of shaft 704. Plate 722 serves as the clamp head in this design. A pair of bearings 726 and 728 enable shaft 704 to oscillate within aligned apertures 730 and 732 at the distal end of saw 702. A threaded cap 734 holds the assembly together.

As shown in FIG. 24, spring 740 is aligned in a plane transverse to the axis of saw 702 and is supported by spring pin 742 within slot 744 of shaft 704. A central bore 746 and aperture 748 in the keeper facilitate cleaning and sterilization of the various components. In the open position shown in FIG. 24, the spring legs rest against bushing 750 which is shaped to provide bearing points for the spring legs as the spring moves towards the closed position shown in FIG. 25. A blade 752 is retained as shown when collet 700 is in the closed position.

The relative orientations of the components shown in the various embodiments may be altered within the scope of this invention. For example, the spring in the embodiment of FIGS. 10 and 11 may be repositioned so that the locking balls are between the spring and the clamping head. Such changes might alter the specific function of some components but would not vary the basic concept disclosed. Furthermore, other arrangements of component parts may provide further embodiments. For example, using any of the embodiments with a motion transferring linkage to make the force of the clamping head be directed perpendicular to the axis of the shaft may enable one to produce a collet in which the activating motion is axially aligned with the shaft while the clamping force is perpendicular thereto, albeit applied at a point spaced from the axis, thereby enabling the saw blade body to be axially aligned with the handpiece but spaced from the axis.

It will be understood by those skilled in the art that numerous improvements and modifications may be made to the preferred embodiment of the invention disclosed herein without departing from the spirit and scope thereof.

What is claimed is:

1. A wrenchless collet for holding a cutting device comprising:

a housing;

clamp means within said housing for holding said cutting device, said clamp means being movable relative to said housing, having an axis and adapted to exert a clamping force on said cutting device parallel to said axis and further comprising:

a first, axially stationary clamping surface;

a second, axially movable clamping surface, said second clamping surface movable to either an open position in which it is spaced from said first clamping surface or a closed position in which it is urged toward said first clamping surface;

bi-stable clamp holding means for selectively holding said clamp means in either said open position or said closed position comprising:

a shaft connected to said second, axially movable clamping surface, said shaft having a first end and a second end, said first and second ends comprising respective first and second shaft pushing members;

a spring biasing means for providing a force;

force transfer means for selectively directing the force of said spring biasing means in either a first direction to hold said second, axially movable clamping surface spaced from said first, axially stationary clamping surface or in a second direction to hold said second, axially movable clamping surface adjacent said first, axially stationary clamping surface.

2. A wrenchless collet according to claim 1 wherein said cutting device is a flat blade having a distal end with a cutting edge and a proximal end with a hub adapted to be retained by said clamp means.

3. A wrenchless collet according to claim 1 further comprising:

said housing having a longitudinally extending opening therethrough and said shaft extending through said opening such that said first and second shaft pushing members situated respectively at said first and second ends of said shaft are each directly manually engageable such that said shaft may be alternately pushed in opposite directions to alternately open and close said clamp means.

4. A wrenchless collet according to claim 3 wherein one of said first or second ends has a different tactile indication than the other.

5. A wrenchless collet according to claim 4 wherein said tactile indication is sized such that one of said first or second ends is larger than the other.

6. A wrenchless collet according to claim 1 wherein said bi-stable clamp holding means comprises:

a flat V-shaped spring comprising a unitary member having a central bight portion and a pair of spring legs extending outwardly from said bight portion;

means for attaching said flat spring to said shaft such that said spring legs lie substantially in a plane parallel to the axis of said shaft and are compressible and expandable toward and away from each other within said plane;

bore means within said housing coaxially situated about said shaft adjacent said spring legs for providing a radially facing surface to urge said spring legs toward each other to frictionally engage said shaft when said clamp means is in said open position;

axial force receiving means adjacent said bore means for receiving an axially directed force from said pair of spring legs as they expand from each other when said clamp means is in said closed position.

7. A wrenchless collet according to claim 6 wherein said flat spring comprises at least one coil loop at said bight portion.

8. A wrenchless collet according to claim 6 wherein said flat spring comprises one of said spring legs extending from that side of said bight portion which is on the same side as said one of said spring legs.

9. A wrenchless collet according to claim 6 wherein said flat spring comprises one of said spring legs extending from that side of said bight portion which is on the opposite side from said one of said spring legs.

10. A wrenchless collet according to claim 6 wherein said shaft is provided with an axially aligned through slot adjacent said first end of said shaft for receiving said flat spring therein while enabling said spring legs to extend radially beyond said slot.

11. A method of selectively attaching a cutting device to a surgical handpiece comprising the steps of:

providing a wrenchless collet having a first clamping surface member and a second clamping surface member, said members being relatively movable between a closed position wherein they are aligned such that a cutting device may be held by said members and an open position wherein they are spaced and a cutting device may be inserted or removed therefrom;

providing means to hold said wrenchless collet either open or closed;

providing a user accessible means secured to said first clamping surface member to urge said first clamping surface member either toward or away from said second clamping surface member;

selectively opening said wrenchless collet by linearly pushing said user accessible means in a first linear direction to move said first clamping surface member axially in one direction;

selectively closing said wrenchless collet by linearly pushing said user accessible means in a second linear direction to move said first clamping surface member axially in a direction opposite to said one direction.

12. A method according to claim 11 wherein said user accessible means is a shaft having opposed ends, said shaft secured to said first clamping surface member, further comprising the steps of activating said user accessible member by pushing said shaft in one axial direction or the other.

13. A method according to claim 12 wherein said means to hold said wrenchless collet comprises a bi-stable spring means for providing in one bi-stable state an axially directed first force in a first direction to hold said collet either open or closed and further comprising the step of exerting an axially directed second force in a second direction to overcome said first force to place said spring means in the other bi-stable state.

* * * * *

UNITED STATES PATENT AND TRADEMARK OFFICE
CERTIFICATE OF CORRECTION

PATENT NO. : 5,729,904
DATED : MARCH 24, 1998
INVENTOR(S) : A. FRANK TROTT

It is certified that error appears in the above-identified patent and that said Letters Patent are hereby corrected as shown below:

Title page, item [54] and column 1, lines 1-2
WRENCHLESS COLLET FOR SURGICAL BLADE

Signed and Sealed this

Second Day of June, 1998

Attest:

BRUCE LEHMAN

*Attesting Officer*  *Commissioner of Patents and Trademarks*